United States Patent [19]

Hertel et al.

[11] Patent Number: 4,775,540

[45] Date of Patent: Oct. 4, 1988

[54] PREPARATION OF POURABLE CHOLINE CHLORIDE/SILICA POWDERS

[75] Inventors: Otto Hertel, Ludwigshafen; Gerhard Jeschek, Gruenstadt; Walter Klink, Birkenheide; Wolfgang Koernig, Dossenheim; Theodor Weber, Ludwigshafen; Fritz Rateike, Lampertheim, all of Fed. Rep. of Germany

[73] Assignee: BASF Aktiengesellschaft, Ludwigshafen, Fed. Rep. of Germany

[21] Appl. No.: 33,849

[22] Filed: Apr. 3, 1987

Related U.S. Application Data

[63] Continuation of Ser. No. 711,206, Mar. 13, 1985, abandoned.

[30] Foreign Application Priority Data

Mar. 13, 1984 [DE] Fed. Rep. of Germany ....... 3409063

[51] Int. Cl.$^4$ .............................................. A23K 1/175
[52] U.S. Cl. ...................................... 426/74; 426/471; 426/648; 426/807
[58] Field of Search ................... 426/648, 74, 72, 471, 426/807

[56] References Cited

U.S. PATENT DOCUMENTS

| 2,472,663 | 6/1949 | Kleine et al. ................... 426/807 X |
| 2,765,231 | 10/1956 | Plitt ....................................... 426/72 |
| 2,879,161 | 3/1959 | Valentine et al. ...................... 99/2 |
| 2,912,331 | 11/1959 | Turner et al. ........................ 426/72 |
| 2,970,911 | 2/1961 | Lorz ...................................... 426/72 |
| 2,986,571 | 5/1961 | Ohodaira ........................ 426/807 X |
| 3,244,527 | 4/1966 | Baker .................................... 426/74 |
| 3,356,569 | 12/1967 | Nicodemus et al. .................. 426/72 |
| 4,519,961 | 5/1985 | Schumacher et al. ............... 264/4.6 |

FOREIGN PATENT DOCUMENTS

| 0074050 | 3/1983 | European Pat. Off. . |
| 2518426 | 6/1983 | France . |
| 1619865 | 3/1971 | Fed. Rep. of Germany . |
| 1692417 | 1/1972 | Fed. Rep. of Germany . |
| 2209477 | 9/1973 | Fed. Rep. of Germany . |
| 84552 | 9/1971 | German Democratic Rep. . |
| 6704009 | 9/1968 | Netherlands . |
| 1412204 | 10/1975 | United Kingdom . |

OTHER PUBLICATIONS

Ullmanns Encyklopädie der technischen Chemie, 4th edition, vol. 21, p. 462 et seq.
Chem. Abs. vol. 81, No. 5, Aug. 5, 1974, p. 384, #25051c.
Copy of European Search Report 85 10 2542.

Primary Examiner—R. B. Penland
Attorney, Agent, or Firm—Keil & Weinkauf

[57] ABSTRACT

A process for the preparation of pourable choline chloride/silica powders by mixing silica with choline chloride and, where appropriate, drying this mixture, wherein spray-dried or fluidized bed-dried silica which has a particle size of from 30 to 250 μm is mixed with an aqueous choline chloride solution which contains from 70 to 80% by weight, based on the solution, of choline chloride and is at from 40° to 80° C., thereafter from 0.05 to 0.4% by weight, based on the mixture, of magnesium stearate or calcium stearate is added and, if appropriate, the resulting mixture is dried.

6 Claims, No Drawings

PREPARATION OF POURABLE CHOLINE CHLORIDE/SILICA POWDERS

This application is a continuation of application Ser. No. 711,206, filed on Mar. 13, 1985, now abandoned.

The present invention relates to a novel process for the preparation of pourable choline chloride/silica powders by mixing silica with an aqueous choline chloride solution and adding magnesium stearate or calcium stearate.

Choline chloride is an important constituent of mixed animal feeds. Predominantly, it is employed as a powder, either of choline chloride as such or of choline chloride applied to a carrier. Carriers used include silica or organic carriers, for example corn cob powder or rice husks.

In the choline chloride powders applied to a carrier, the concentration of choline chloride is in general about 50% by weight, but powders with higher or lower concentrations than this value are also known and are commercially available.

Products in which the carrier is silica are, in the main, absorbates and as a rule contain from 15 to 25% by weight of residual water. Products employing organic carriers are usually dried and contain about 1-2% by weight of residual water.

Since choline chloride is hygroscopic, the said choline chloride powders tend to cake and hence become difficult to pour when they come into contact with moisture, for example from the atmosphere. Freshly manufactured products also in most cases are not readily pourable, because of containing residual water on the particle surface.

However, good pourability is absolutely essential for further conversion to feeds, especially in the case of premixes. Moreover, it is necessary to be sure that even if packages containing choline chloride powder are left open for several hours, the powder has very little tendency to cake and thus remains easily pourable.

It is known that the undesired caking of carrier-free choline chloride powders can be repressed by adding substantial amounts of stearic acid salts.

NL-A-No. 6 704 009 proposes that in the preparation of carrier-free choline chloride powder sodium stearate be added in a proportion of about 20% by weight, based on the mixture.

DD-A-No. 84 552 discloses stabilizing carrier-free choline chloride with magnesium stearate or calcium stearate, the proportion of stearates in the examples being from 2.9 to 4.8% by weight, based on the mixture.

It is an object of the present invention to provide a process for the preparation of pourable and noncaking choline chloride powders which employ a silica carrier, which process also avoids having to add substantial amounts of expensive stearic acid salts.

We have found that this object is achieved and that pourable choline chloride/silica powders are obtained in an advantageous manner by mixing silica with choline chloride and, where appropriate, drying this mixture, wherein spray-dried or fluidized bed-dried silica which has a particle size of from 30 to 250 μm is mixed with an aqueous choline chloride solution which contains from 70 to 80% by weight, based on solution, of choline chloride and is at from 40° to 80° C., thereafter from 0.05 to 0.4% by weight, based on the mixture, of magnesium stearate or calcium stearate is added and, if appropriate, the resulting mixture is dried.

This result is surprising since, as already mentioned, in the case of carrier-free choline chloride the pourability is improved only upon addition of substantial amounts of stearates, and the addition of stearates to choline chloride powders employing an organic carrier has no particular effect on pourability.

In the process according to the invention, silica is used as the carrier. Precipitated silicas are suitable for this purpose. They are obtained by reacting an aqueous alkali metal silicate solution (for example a waterglass solution) with a mineral acid (for example sulfuric acid or hydrochloric acid), followed by filtration and spray drying or fluidized bed drying (cf. Ullmanns Encyklopädie der technischen Chemie, 4th edition, Volume 21, page 462 et seq.). The silicas should have a particle size of from 30 to 250 μm, it being particularly advantageous if more than 50% by weight, especially more than 60% by weight, of the silicas has a particle size of from 50 to 160 μm. The water of content of the silicas should be from 4 to 6% by weight, preferably from 4.3 to 6% by weight, and the tap density should be from 240 to 300 g/l.

Commercial precipitated silicas which conform to these criteria include, for example, those sold under the name ®Sipernat (a trademark, registered in the Federal Republic of Germany, of Degussa, Frankfurt).

In preparing the mixture, an aqueous choline chloride solution is used which contains from 70 to 80% by weight, preferably from 77 to 80% by weight, and especially 78% by weight—in each case based on solution—of choline chloride.

The aqueous choline chloride solution and the silica are mixed in a weight ratio such that after completion of mixing a water-containing choline chloride/silica powder is obtained in which the choline chloride content is from 40 to 51% by weight, preferably from 45 to 51% by weight and especially from 50 to 51% by weight, in each case based on the mixture.

In principle it is also possible to use this method to obtain powders in which the choline chloride content is less than 40% by weight.

Before carrying out the mixing, the aqueous chlorine choline solution is heated to 40°-80° C., preferably 50°-70° C. and especially 60° C.

The mixing process is carried out in mixing apparatus known per se. The silica, which is usually at 20°-30° C., is introduced first, and the heated aqueous choline chloride solution is then added over a period of from 1 to 4 hours. Post-mixing usually lasts from 10 to 40 minutes. Thereafter, from 0.05 to 0.4% by weight, preferably from 0.1 to 0.2% by weight, in each case based on the mixture, of magnesium stearate or calcium stearate is added.

The stearates are usually added undiluted as a finely milled powder. After this addition, post-mixing is again carried out, for about 5-30 minutes.

Using the process according to the invention it is also possible to produce dried choline chloride/silica powders containing less than 1.5% by weight of water and 40-80% by weight, preferably 51-80% by weight, of choline chloride.

To do so, the aqueous choline chloride solution and silica are mixed in the appropriate weight ratio, magnesium stearate or calcium stearate is added and after completion of the mixing process the mixture is spray-dried or fluidized bed-dried.

Another possible method is to spray the aqueous choline chloride solution onto the silica, add magnesium stearate or calcium stearate to this mixture and, after completion of the mixing process, drying the mixture at from 110° to 150° C.

The choline chloride/silica powders produced by the process according to the invention possess excellent flow properties, good shelf life and little tendency to cake.

To assess the pourability, glass vessels with a conical outlet are used. The diameter of the outlet orifice is from 0.5 to 5 cm. The pourability is determined as follows: 100 g of choline chloride powder are required to flow freely, without being shaken, through the orifice. If this proves possible at an orifice diameter of 0.5 cm, the pourability is described as very good. If an orifice diameter of from 0.6 to 2 cm is required, the pourability is adjudged good, while if an orifice diameter of more than 3 cm is required, the pourability is considered inadequate.

A product is described as having a good shelf life if it is still readily pourable after having been stored for 24 hours at room temperature and at about 80% relative atmospheric humidity.

The Examples which follow illustrate the invention.

Example 1

5 kg of a 77.87% strength by weight aqueous choline chloride solution, which had been preheated to 60° C., were added in the course of 2 hours to 2.75 kg of silica (Sipernat 22), having a particle size distribution within the range from 30 $\mu$m to 195 $\mu$m and a water content of 4.7% by weight, in a mixer. Mixing was then continued for 20 minutes. The pourability at this stage was inadequate (orifice diameter: 4 cm).

After the addition of 9.75 g of calcium stearate, with 8 minutes' further mixing, the pourability was very good (orifice diameter: 0.5 cm). The choline chloride content of the product was 50.2% by weight and the water content 22% by weight. The product had a good shelf life and retained good pourability (orifice diameter: 2 cm) after 24 hours' standing in air at 80% relative humidity.

Example 2

5 kg of a 77.87% strength by weight aqueous choline chloride solution, which had been preheated to 60° C., were added in the course of 2 hours to 2.75 kg of silica (Sipernat 22), having a particle size distribution within the range from 30 $\mu$m to 195 $\mu$m and a water content of 4.7% by weight, in a mixer. Mixing was then continued for 15 minutes. The pourability at this stage was inadequate (orifice diameter: 4 cm).

After addition of 10.5 g of magnesium stearate, with 8 minutes' further mixing, the pourability was very good (orifice diameter: 0.5 cm). The choline chloride content of the product was 50.1% by weight and the water content 21.9% by weight. The product had a good shelf life and retained good pourability (orifice diameter: 2 cm) after 24 hours' standing in air at 75% relative humidity.

Examples 3 And 4 (Comparative Experiments)

The procedure followed was similar to Examples 1 and 2 except that the temperature of the choline chloride solution was in each case only 25° C. After mixing, the pourability of both products was found to be inadequate (orifice diameter: >3 cm).

Example 5 (Comparative Experiment)

5 kg of a 77.87% strength by weight aqueous choline chloride solution, which had been preheated to 60° C., were added in the course of 2 hours to 2.75 kg of silica, having a particle size distribution within the range from 20 $\mu$m to 380 $\mu$m and a water content of 4% by weight, in a mixer. Mixing was then continued for 20 minutes. The pourability at this stage was inadequate (orifice diameter: >5 cm). The product hardly flowed.

The pourability could not be improved even by adding 9.75 g of calcium stearate and mixing for a further 10 minutes.

We claim:

1. A process for preparing pourable choline chloride/silica powders consisting essentially of the following sequential steps:
   a. forming a water-containing choline chloride/silica powder by mixing spray dried or fluidized bed dried silica having a particle size of from 30 to 250 $\mu$m with an aqueous choline chloride solution having a solids content of from 70 to 80% by weight, the silica and aqueous choline chloride solution being in a weight ratio such that the mixture resulting from said mixing has a choline chloride content of from 40 to 51 percent by weight, said mixing operation being conducted by initially adding the silica to a mixing device followed by addition of the aqueous choline chloride solution over a period of 1 to 4 hours, which solution has been pre-heated to a temperature of from 40° to 80° C., and
   b. adding to the powdered mixture formed in step (a) from 0.05 to 0.4% by weight, based on said mixture, of magnesium stearate or calcium stearate followed by a mixing of these ingredients.

2. A process as claimed in claim 1, wherein an aqueous choline chloride solution at from 50° to 70° C. is used.

3. A process as claimed in claim 1, wherein the aqueous choline chloride solution containing from 77 to 80% by weight of choline chloride is used.

4. A process as claimed in claim 1, wherein a spray-dried or fluidized bed-dried silica, of which more than 50% by weight has a particle size of from 50 to 160 $\mu$m, is used.

5. A process as claimed in claim 1, wherein a spray-dried or fluidized bed-dried silica containing from 4 to 6% by weight of water is used.

6. A process as claimed in claim 1, wherein from 0.1 to 0.2% by weight of magnesium stearate or calcium stearate is added.

* * * * *